US00PP26928P2

(12) United States Plant Patent
Kolster

(10) Patent No.: US PP26,928 P2
(45) Date of Patent: Jul. 12, 2016

(54) ***HYDRANGEA* PLANT NAMED 'KOLMAVESU'**

(50) Latin Name: *Hydrangea paniculata*
Varietal Denomination: Kolmavesu

(71) Applicant: Peter R. Kolster, Boskoop (NL)

(72) Inventor: Peter R. Kolster, Boskoop (NL)

(73) Assignee: Kolster Holding B.V., Boskoop (NL)

( * ) Notice: Subject to any disclaimer, the term of this patent is extended or adjusted under 35 U.S.C. 154(b) by 177 days.

(21) Appl. No.: 13/999,248

(22) Filed: Jan. 31, 2014

(51) Int. Cl.
*A01H 5/02* (2006.01)

(52) U.S. Cl.
USPC ..... Plt./250

(58) Field of Classification Search
USPC ..... Plt./250
See application file for complete search history.

*Primary Examiner* — Anne Grunberg
(74) *Attorney, Agent, or Firm* — C. A. Whealy

(57) ABSTRACT

A new and distinct cultivar of *Hydrangea* plant named 'Kolmavesu', characterized by its upright and relatively compact plant habit; strong stems; freely flowering habit; and large upright conical inflorescences with white-colored sterile flowers that become red purple in color in mid-August in The Netherlands.

4 Drawing Sheets

Botanical designation: *Hydrangea paniculata.*
Cultivar denomination: 'KOLMAVESU'.

BACKGROUND OF THE INVENTION

The present invention relates to a new and distinct cultivar of *Hydrangea* plant, botanically known as *Hydrangea paniculata* and hereinafter referred to by the name 'Kolmavesu'.

The new *Hydrangea* plant is a product of a planned breeding program conducted by the Inventor in Boskoop, The Netherlands. The objective of the breeding program is to create new relatively compact *Hydrangea* plants that have a freely flowering habit with attractive inflorescence form and flower color.

The new *Hydrangea* plant originated from an open-pollination in August, 2006 in Boskoop, The Netherlands of *Hydrangea paniculata* 'DVP Pinky', disclosed in U.S. Plant Pat. No. 16,166, as the female, or seed parent with an unknown selection of *Hydrangea paniculata* as the male, or pollen, parent. The new *Hydrangea* plant was discovered and selected by the Inventor as a single flowering plant within the progeny of the stated open-pollination in a controlled greenhouse environment in Boskoop, The Netherlands in 2011.

Asexual reproduction of the new *Hydrangea* plant by vegetative cuttings in a controlled greenhouse environment in Boskoop, The Netherlands since 2011 has shown that the unique features of this new *Hydrangea* plant are stable and reproduced true to type in successive generations.

SUMMARY OF THE INVENTION

Plants of the new *Hydrangea* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Kolmavesu'.

These characteristics in combination distinguish 'Kolmavesu' as a new and distinct *Hydrangea* plant:

1. Upright and relatively compact plant habit.
2. Strong stems.
3. Freely flowering habit.
4. Large upright conical inflorescences with white-colored sterile flowers that become red purple in color in mid-August in The Netherlands.

Plants of the new *Hydrangea* differ primarily from plants of the female parent, 'DVP Pinky', in the following characteristics:

1. Plants of the new *Hydrangea* are more compact than plants of 'DVP Pinky'.
2. Plants of the new *Hydrangea* are more upright than and not as outwardly spreading as plants of 'DVP Pinky'.

Plants of the new *Hydrangea* can be compared to plants of *Hydrangea paniculata* 'Bokratorch', disclosed in U.S. Plant Pat. No. 21,292. Plants of the new *Hydrangea* differ primarily from plants of 'Bokratorch' in the following characteristics:

1. Plants of the new *Hydrangea* are more upright than and not as outwardly spreading as plants of 'Bokratorch'.
2. Plants of the new *Hydrangea* have smaller leaves than plants of 'Bokratorch'.
3. Flowers of plants of the new *Hydrangea* change color in mid-August whereas flowers of plants of 'Bokratorch' change color in late August in The Netherlands.

BRIEF DESCRIPTION OF THE PHOTOGRAPHS

The accompanying colored photographs illustrate the unique appearance of the new *Hydrangea* plant showing the colors as true as it is reasonably possible to obtain in colored reproductions of this type. Colors in the photographs may differ from the color value cited in the detailed botanical description which accurately describe the colors of the new *Hydrangea* plant.

The photograph on the first sheet comprises a side perspective view of a typical plant of 'Kolmavesu' grown in a container.

The photograph on the second sheet is a close-up view of typical leaves of 'Kolmavesu'.

The photograph on the third sheet is a close-up view of a typical inflorescence of 'Kolmavesu'.

The photograph on the fourth sheet is a close-up view of a typical inflorescence of 'Kolmavesu' after the color change.

DETAILED BOTANICAL DESCRIPTION

Plants used in the aforementioned photographs and in the following description were grown during the summer and early autumn in 28-cm containers in an outdoor nursery in Boskoop, The Netherlands and under cultural conditions typical of commercial *Hydrangea* production. During the production of the plants, day temperatures ranged from 12° C. to 23° C. and night temperatures ranged from 3° C. to 15° C. Plants of the new *Hydrangea* were four years old when the photographs and description were taken. In the following description, color references are made to The Royal Horticultural Society Colour Chart, 2007 Edition, except where general terms of ordinary dictionary significance are used.

Botanical description: *Hydrangea paniculata* 'Kolmavesu'.

Parentage:

*Female, or seed, parent.*—*Hydrangea paniculata* 'DVP Pinky', disclosed in U.S. Plant Pat. No. 16,166.

*Male, or pollen, parent.*—Unknown selection of *Hydrangea paniculata*, not patented.

Propagation:

*Method.*—By softwood cuttings.

*Time to initiate roots, summer.*—About four weeks at temperatures about 20° C.

*Time to produce a rooted young plant, summer.*—About three months at temperatures about 20° C.

*Root description.*—Medium in thickness, fibrous; creamy white in color.

*Rooting habit.*—Moderately freely branching; medium density.

Plant description:

*Plant and growth habit.*—Upright and relatively compact plant habit; somewhat narrowly inverted triangle; strong erect stems; freely branching habit with about ten lateral branches developing per plant, pinching enhances lateral branch development; moderately vigorous growth habit.

*Plant height.*—About 106 cm.

*Plant diameter or area of spread.*—About 68.5 cm.

*Lateral branches.*—Length: About 81.3 cm. Diameter: About 6 mm. Internode length: About 6.8 cm. Texture, developing: Pubescent. Texture, fully developed: Smooth, glabrous. Angle: About 15° from vertical. Strength: Strong. Color, developing: Close to 183C. Color, developed: Close to 200D.

Leaf description:

*Arrangement.*—Opposite, simple.

*Length.*—About 12.1 cm.

*Width.*—About 6.1 cm.

*Shape.*—Ovate to narrowly ovate.

*Apex.*—Apiculate.

*Base.*—Short attenuate.

*Margin.*—Serrate.

*Texture, upper surface.*—Slightly rugose; sparsely pubescent.

*Texture, lower surface.*—Slightly rugose; pubescent.

*Luster, upper surface.*—Glossy.

*Luster, lower surface.*—Slightly glossy.

*Venation pattern.*—Pinnate.

*Color.*—Developing leaves, upper surface: Close to 143A. Developing leaves, lower surface: Between 144A and 146C. Fully expanded leaves, upper surface: Darker than between 143A and 146A; venation, close to 152B. Fully expanded leaves, lower surface: Between 138A and 147B; venation, close to 148D and towards the base, tinged with close to 182B to 182C.

*Petioles.*—Length: About 2.5 cm. Diameter: About 3 mm. Texture, upper surface: Pubescent. Texture, lower surface: Smooth, glabrous. Color, upper surface: Close to 178A to 178B. Color, lower surface: Close to 182A to 182B.

Flower description:

*Flower type and habit.*—Single fertile and sterile flowers arranged on large upright conical panicles; panicles terminal; sterile and fertile flowers face upright to outwardly.

*Fragrance.*—Very faint; sweet and pleasant.

*Natural flowering season.*—Continuous flowering from summer to mid-autumn in The Netherlands.

*Flower longevity, fertile flowers.*—About one week on the plant; fertile flowers not persistent.

*Flower longevity, sterile flowers.*—About three weeks on the plant; sterile flowers persistent.

*Quantity of flowers.*—Freely flowering habit; about 900 fertile flowers and about 100 sterile flowers develop per panicle.

*Panicle height.*—About 17 cm.

*Panicle diameter.*—About 11.8 cm.

*Flower buds, fertile flowers.*—Length: About 3 mm. Diameter: About 2.5 mm. Shape: Broadly obovate. Color: Close to 145B; towards the apex, close to 186B to 186C.

*Flower buds, sterile flowers.*—Length: About 4 mm. Diameter: About 2 mm. Shape: Obovate. Color: Close to 144B to 144C.

*Fertile flowers.*—Diameter: About 5 mm. Depth: About 5 mm. Shape: Rotate. Petals: Quantity and arrangement: Five in a single whorl. Length: About 1.5 mm. Width: About 1.5 mm. Shape: Ovate. Apex: Acute. Base: Broadly cuneate. Margin: Entire. Texture, upper and lower surfaces: Smooth, glabrous. Color: When opening and fully opened, upper surface: Close to 145D. When opening and fully opened, lower surface: Close to 145D. Sepals: Quantity and arrangement: Five in a single whorl. Length: About 0.5 mm. Width: About 1 mm. Shape: Short triangular. Apex: Broadly acute. Base: Broadly cuneate. Margin: Entire. Texture, upper and lower surfaces: Smooth, glabrous. Color: When opening and fully opened, upper surface: Close to 145C. When opening and fully opened, lower surface: Close to 145C. Pedicels: Length: About 2 mm. Diameter: About 0.5 mm. Strength: Moderately strong. Texture: Smooth, glabrous. Color: Close to 145B.

*Reproductive organs.*—Stamens: Quantity per flower: Ten. Filament length: About 2.5 mm. Filament color: Close to NN155D. Anther shape: Double reniform. Anther length: About 0.6 mm. Anther color: Close to 152C. Pollen amount: Scarce. Pollen color: Close to 158D. Pistils: Quantity per flower: Two, occasionally three. Pistil length: About 2 mm. Stigma shape: Flattened. Stigma color: Close to 145D. Style length: About 1 mm. Style color: Close to 144B. Ovary color: Close to 144B.

*Sterile flowers.*—Shape: Rotate, cruciform. Diameter: About 2.7 cm. Depth (height): About 1 cm. Petals: Quantity and arrangement: Four in a single whorl.

Length: About 2.5 mm. Width: About 1.5 mm. Shape: Ovate, concave. Apex: Acute. Base: Cuneate. Margin: Entire. Texture, upper and lower surfaces: Smooth, glabrous. Color: When opening and fully opened, upper surface: Close to 155A; distal half, tinged with close to 186D. When opening and fully opened, lower surface: Close to 155A; distal half, close to 61B. Sepals: Quantity and arrangement: Five in a single whorl. Length: About 1.6 cm. Width: About 1.1 cm. Shape: Obovate to broadly elliptic, occasionally ovate. Apex: Obtuse to rounded. Base: Cuneate. Margin: Entire. Texture, upper and lower surfaces: Smooth, glabrous. Color: When opening, upper and lower surfaces: Close to 155B to 155C. Fully opened, upper surface: Close to 157A to 157B; towards the margins and apex, strongly tinged with close to 70D; with development in mid-August in The Netherlands, color becomes closer to 59A to 59B and 187D. Fully opened, lower surface: Close to 157A to 157B; towards the margins and apex, strongly tinged with close to 65A; with development in mid-August in The Netherlands, color becomes closer to 187D. Pedicels: Length: About 1.9 cm. Diameter: About 1 mm. Strength: Moderately strong. Angle: About 40° from stem axis. Texture: Moderately pubescent. Color: Close to 155D.

*Reproductive organs.*—Stamens: Quantity per flower: Eight. Filament length: About 1 mm. Filament color: Close to 155D. Anther shape: Double reniform. Anther length: About 0.5 mm. Anther color: Close to 151A. Pollen amount: None observed. Pistils: Quantity per flower: Three. Pistil length: About 2 mm. Stigma shape: Flattened. Stigma color: Close to 145D. Style length: About 1 mm. Style color: Close to 144B. Ovary color: Close to 144B. Fruits and seeds: Fruit and seed development have not been observed on plants of the new *Hydrangea.*

Disease & pest resistance: Plants of the new *Hydrangea* have not been observed to be resistant to pathogens or pests common to *Hydrangea* plants.

Temperature tolerance: Plants of the new *Hydrangea* have been shown to be tolerant to temperatures ranging from about −30° C. to about 40° C.

It is claimed:

1. A new and distinct *Hydrangea* plant named 'Kolmavesu' as illustrated and described.

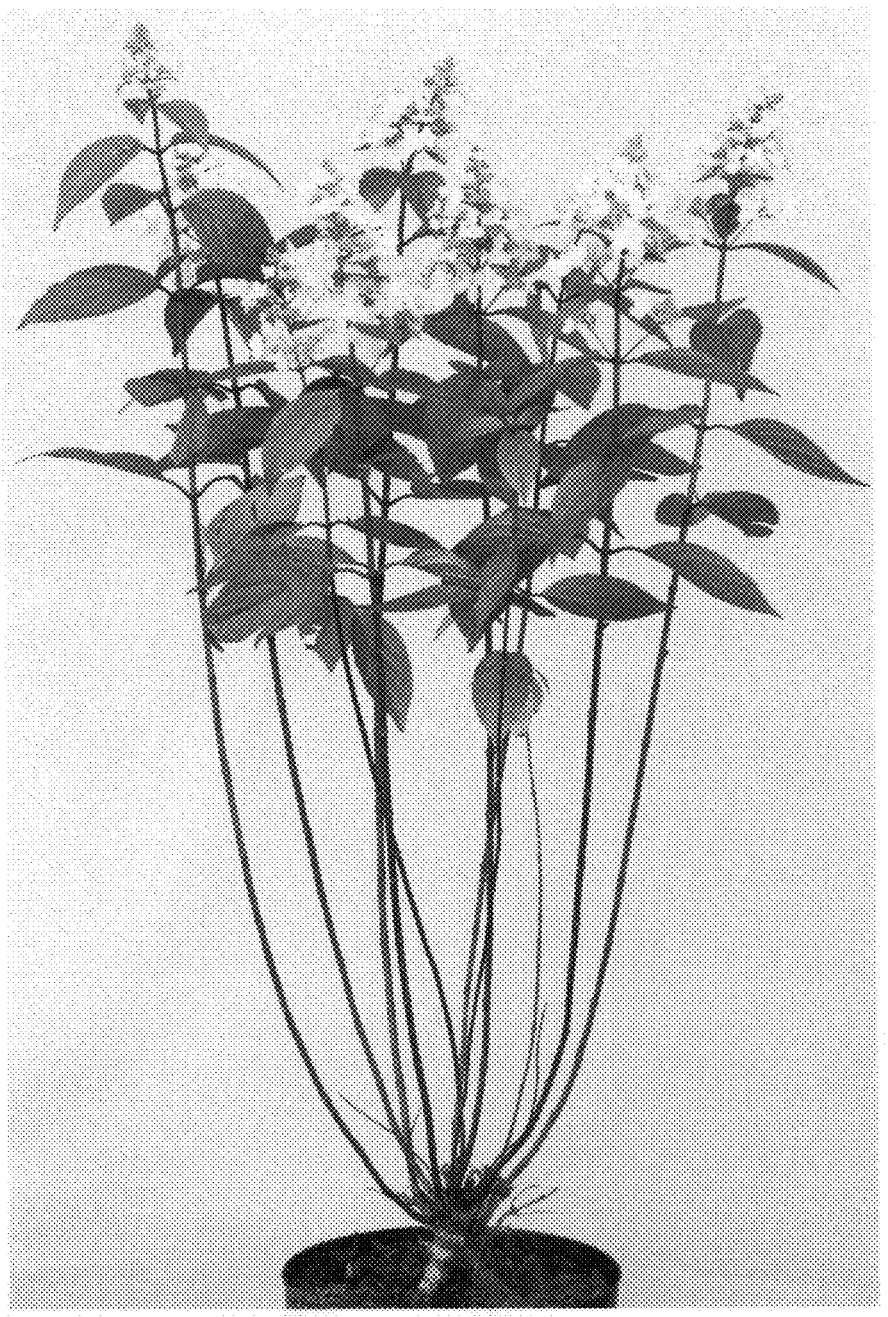

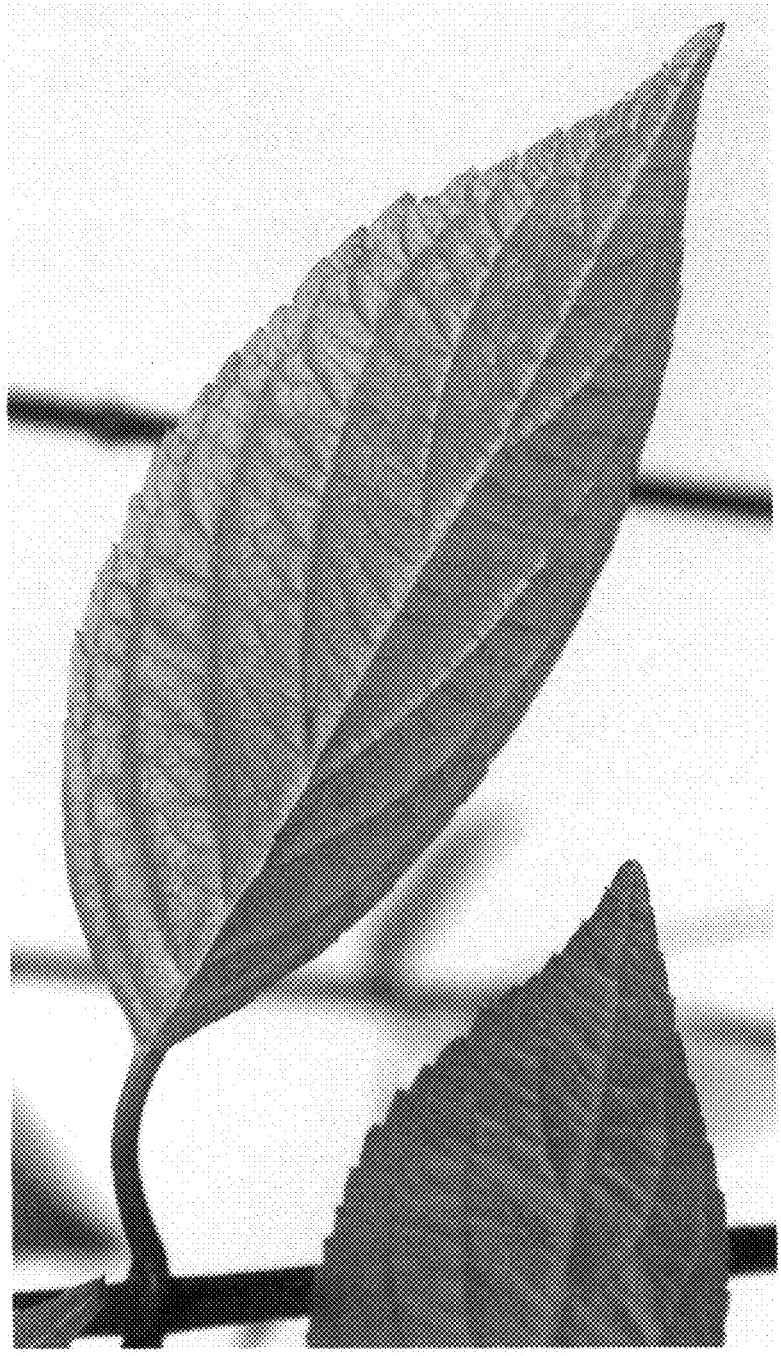

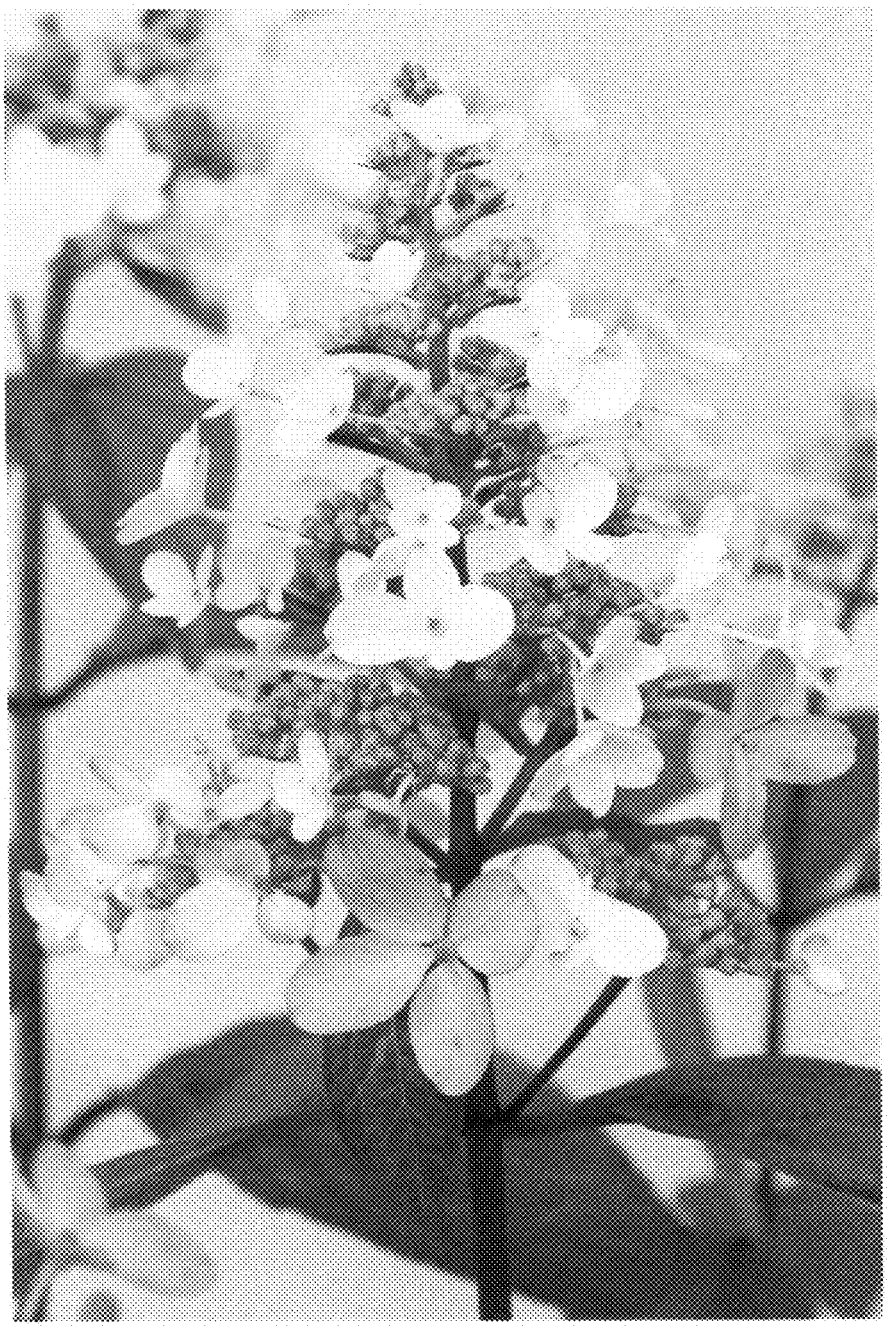

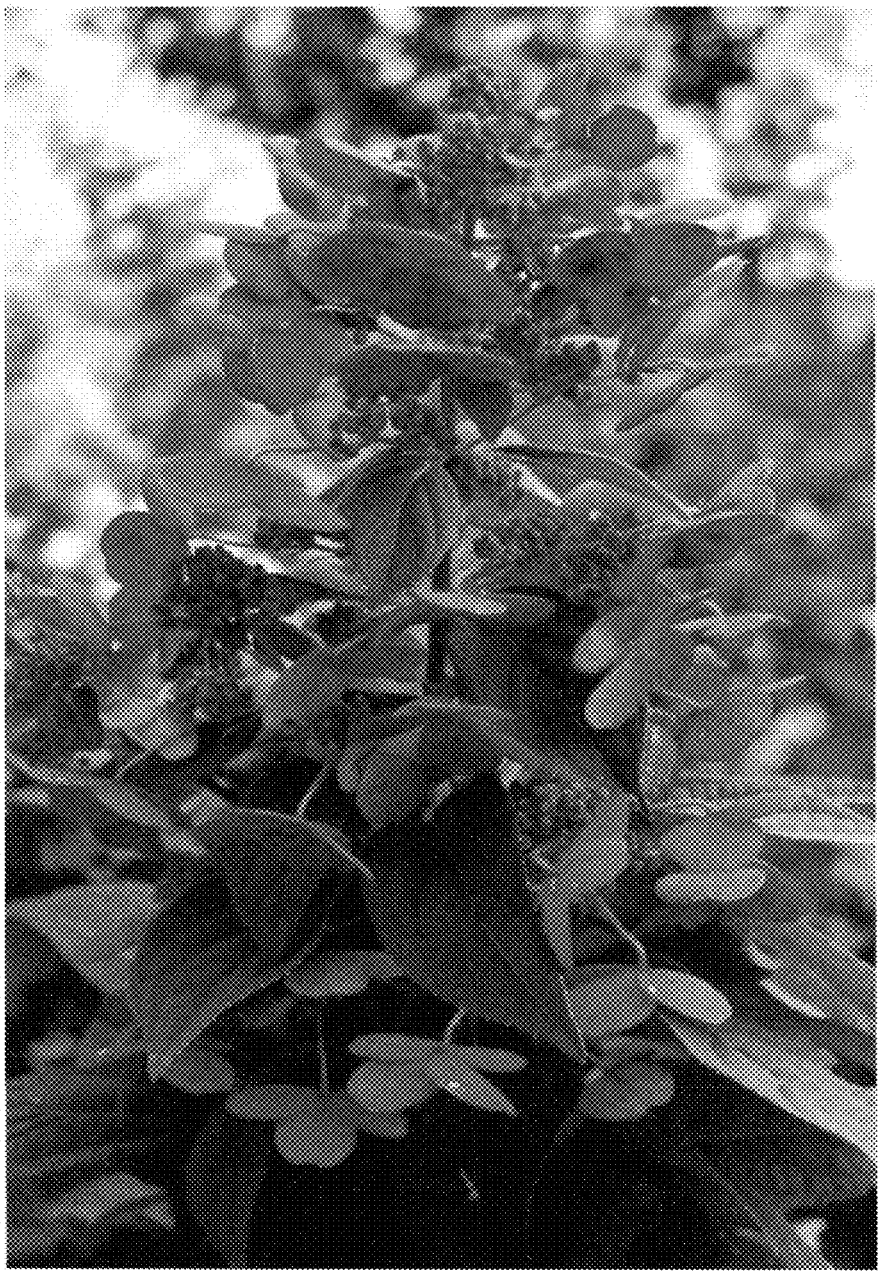

* * * * *